United States Patent [19]

Kraus

[11] 4,214,322
[45] Jul. 29, 1980

[54] LONG-TERM ENDOPROSTHESIS

[76] Inventor: Werner Kraus, 41 Augustenstrasse, Munich, Fed. Rep. of Germany

[21] Appl. No.: 43,775

[22] Filed: May 30, 1979

Related U.S. Application Data

[62] Division of Ser. No. 779,127, Mar. 18, 1977.

[30] Foreign Application Priority Data

Mar. 19, 1976 [DE] Fed. Rep. of Germany ....... 2611744

[51] Int. Cl.² .............................................. A61F 1/24
[52] U.S. Cl. ...................................... 3/1.91; 3/1.912; 128/82.1; 128/92 C; 128/419 F; 433/173; 433/175
[58] Field of Search ................................. 3/1.9–1.913; 128/82.1, 92 C, 92 CA, 92 G, 419 F; 433/173, 175

[56] References Cited

U.S. PATENT DOCUMENTS

| | | | |
|---|---|---|---|
| 3,745,995 | 7/1973 | Kraus | ................................... 128/82.1 |
| 3,820,534 | 6/1974 | Kraus et al. | .......................... 3/1.9 X |
| 3,964,473 | 6/1976 | Wickham et al. | ........... 128/419 F X |

Primary Examiner—Ronald L. Frinks
Attorney, Agent, or Firm—Edwin E. Greigg

[57] ABSTRACT

A long-term endoprosthesis in which a relatively large part of the surface, which in the implanted condition makes contact with the bone of the wearer of the implant, is provided with electrodes. These electrodes are connected with a source of a low frequency electrical voltage and are so arranged that they alternate with relatively short spacings in the contact zone. The electrode spacing preferably decreases in size in accordance with the size of the mechanical area loading on the corresponding part of the contact area, that is to say, the greater the loading, the smaller the spacing.

5 Claims, 22 Drawing Figures

LONG-TERM ENDOPROSTHESIS

This is a division of application Ser. No. 779,127 filed Mar. 18, 1977.

BACKGROUND OF THE INVENTION

1. The prior art

The U.S. Pat. Nos. 3,387,880, 3,820,534 and 3,918,440 and the corresponding U.K. Pat. No. 1,311,519, 1,393,701 and 1,393,703 describe arrangements for the healing of compound bone fractures, comminuted fractures in conjunction with damage to soft parts of the body, pathological fractures, spontaneous fractures and for overcoming difficulties in healing due to pseudoarthroses, osteomyelitides and the like, in the case of which a magnetic field is induced to produce bioelectric potentials and currents in the defective tissue and as a result to accelerate regeneration and to enable healing to take place in cases which are resistant to therapy.

For this treatment a coil is implanted in the vicinity of the fracture which represents the secondary inductance of a transformer and it is associated with a osteosynthetic part of a conventional type as for example a support plate, a pin driven into the marrow of the bone or even a joint prosthesis, or a coil can be incorporated in such an osteosynthetic part of a joint prosthesis. The inducing magnetic field is excited in a coil surrounding the diseased tissue region. The coil is supplied from a low frequency generator with current and it constitutes the primary inductance of the transformer. The low frequency magnetic field of the coil pervades the whole tissue region, which comprises the bone defect and induces an electrical voltage in the implanted coil, the voltage being caused to act in the tissue via electrodes in the form of bone screws, wires or via metallic foil arranged at the surface of an implantate in an insulated manner.

Experiments on animals and numerous clinical applications of this technique show that in the tissue pervaded by the magnetic field the bone formation prompted by the low frequency alternating electric potentials begins in the immediate neighborhood of the electrodes and continues in the tissue region between the electrodes. As has been shown by histological analysis, the stimulated growth of the bone follows the gradients of the electric potential. If the electrodes extend through the gap of a fracture, generally perpendicular to the fracture surfaces, "bone bridges" form under the influence of the induced potentials and they can quickly take over the supporting fuction of the osteosynthetic elements. As soon as the load carrying capacity of the newly formed bone is sufficient, the whole osteosynthetic part can be removed from the tissue together with the implanted coil and the electrodes.

For bone fracture treatment and bone regeneration experience has shown that a few discrete electrodes, for example two to four electrodes can be used which owing to locally concentrated electric potentials stimulate growth which starts and accelerates regeneration of the tissue. The purpose of the electrodes is a formation of a load carrying bone bridge where the bone is defective. The further conduct of regeneration and consolidation of the bone then takes place under the influence of functional loading in accordance with Wolff's Law.

As regards an implant which is to remain in the tissue for extended periods of time, if possible for the whole of the life of the patient, the requirements applying are in many ways different and they are in effect very much more exacting; the implant is to take over the functions of missing bone components, the support and bearing of an artificial joint or the anchoring of a tooth in the alveolus of the jaw bone.

Metallic implants have not been found suitable for this purpose, since the metal is attacked and not accepted by the tissue. Furthermore ceramic materials developed in more recent times for implantation purposes on the basis of aluminum oxide, quartz, silicon nitride and ceramic compound materials still leave much to be desired. While they have a sufficient mechanical strength and there is a freedom from any substantial attack by body fluids ceramic implant materials have not successfully overcome the problem, as was the case of previously employed metallic implants, of the still insufficient degree of biological tolerance. Even in the case of experiments on animals the process of embedding of, for example, a ceramic joint prosthesis lasts approximately three months despite the high regeneration capabilities of animals. During this time the joint must not be used, that is to say the extremity must be kept still. In the case of accident casualities or aged persons the implant does not become embedded or only does so in a substantially longer period of time. However even periods of one quarter of a year in which the patient must keep the fracture still lead to substantial additional health problems.

Attempts have been made to shorten these times in which the patient must keep still by a special shaping of the implants, for example by the use of a threaded or support rib design, which anchors the implant in the bone with or without the use of a cement. While implants of this type are capable of taking up loads sooner, a functional contact of the implant with the vital tissue is restricted in the case of ceramic prosthesis designed upon these lines to the times applying for metal prosthesis, that is to say on average to approximately 6 to 7 years. An insiduous progressive encapsulation by connective tissue of the implant which is experienced as a foreign body thus leads in the course of time to a painful loosening of the prosthesis. It then becomes necessary to remove the prosthesis and carry out a new implantation, whose life expectancy will, however, be substantially reduced. With the speedy increase in degenerative and accident damage to the human skeleton, which has to be repaired by the implantation of bone prosthesis (at a rate of presently approximately 1500 cases daily) a medicinal and economic problem has been developing on a substantial scale.

SHORT SUMMARY OF THE INVENTION

One aim of the present invention is that of providing an endoprosthesis which is suitable as a long-term implant and whose anchoring in the bone is substantially more reliable and longer lasting than with previously proposed endoprosthesis.

This aim is achieved in accordance with the invention by the measures claimed in claim 1.

The subordinate claims relate to further developments and advantageous forms of long-term endoprosthesis.

In contrast to the above mentioned "electro"-osteosynthetic implants of the prior art, which only remain in the body tissue for the purpose of the growth of new bone until the damaged part of the bone can be loaded again, the endoprosthesis in accordance with the invention have been specifically developed in order to provide a functional, force transmitting and trouble-free bond between the vital bone and the surface of the prosthesis body as rapidly as possible and then to ensure that it lasts for the rest of the patient's life. As has been found to be particularly significant a relatively even biologically active contact extending over a wide area, is produced and maintained between the bone and the prosthesis structure.

LIST OF SEVERAL VIEWS OF THE DRAWINGS

In what follows embodiments of the invention will be described in detail with reference to the accompanying drawings with the explanation of further features, properties and advantages of the long-term endoprosthesis of the invention.

DESCRIPTION OF THE SEVERAL EMBODIMENTS OF THE INVENTION

The long-term endoprosthesis in accordance with the invention comprise preferably and at least on the surface a tissue-compatible ceramic material as for example on the basis of aluminum oxide, silicon dioxide and/or silicon nitride. Furthermore compound materials of metallic or non-metallic filaments can be employed in a non-metallic or metallic matrix.

An important feature of the present long-term endoprosthesis resides in that a relatively large part of the surface, which in the implanted condition makes contact with the bone of the wearer of the implant, is provided with electrodes. The electrodes are preferably disposed throughout at least 50 percent of the surface area of contact. These electrodes are connected with a source of a low frequency electrical voltage and are so arranged that they alternate with relatively short spacings in the contact zone. The electrode spacing preferably decreases in size in accordance with the size of the mechanical area loading on the corresponding part of the contact area, that is to say, the greater the loading, the smaller the spacing. The electrode spacing has a maximum of 10 mm.

The alternating voltage for the electrode can be induced in a conventional manner by an external magnetic alternating field. Since in the case of a long-term implant in accordance with the invention after embedding only relatively small electrical voltages are required in order to keep the bone in contact with the implant "alive" and to ensure a firm seating of the prosthesis, in the present long-term implant measures are preferably taken in order to produce the necessary low frequency alternating voltages automatically during normal use of the endoprothesis. This offers the advantage that no special treatment with a magnetic field generator is required. Preferably however, in addition to the internal alternating voltage generator, as a particularly convenient feature, as a part of this internal alternating voltage generator, a receiving coil is provided, in which a voltage can be induced from outside, so that for the embedding or growing-in period a higher alternating voltage can be caused to act at the electrodes. For keeping the tissue vital around the implantate structure it has been found in accordance with the invention that voltages are sufficient which produce average field strengths in the order of magnitude of 1.0 to 10 mV/cm.

Figure 1:
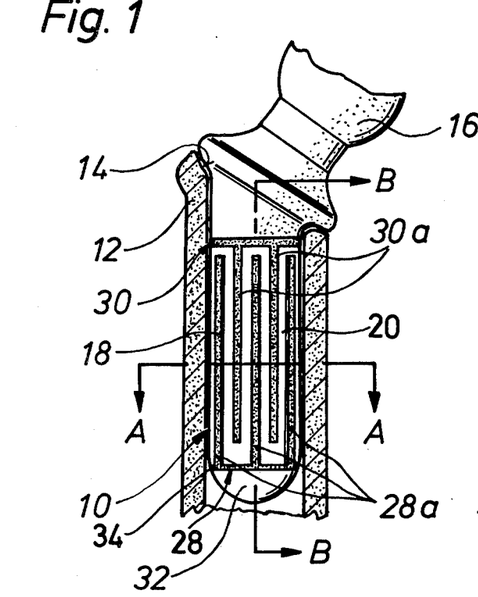
FIG. 1 is a side view of a hip joint head prosthesis in accordance with one embodiment of the invention.
Figure 2A:
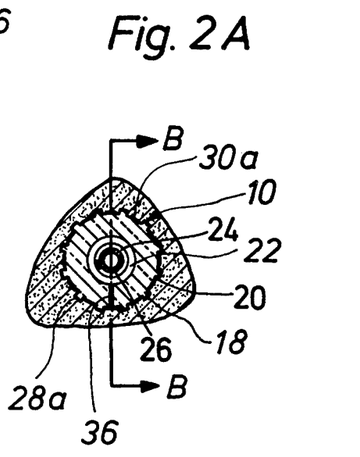
FIG. 2A shows a cross-section in a plane A—A of FIG. 1.
Figures 2B, 2C:
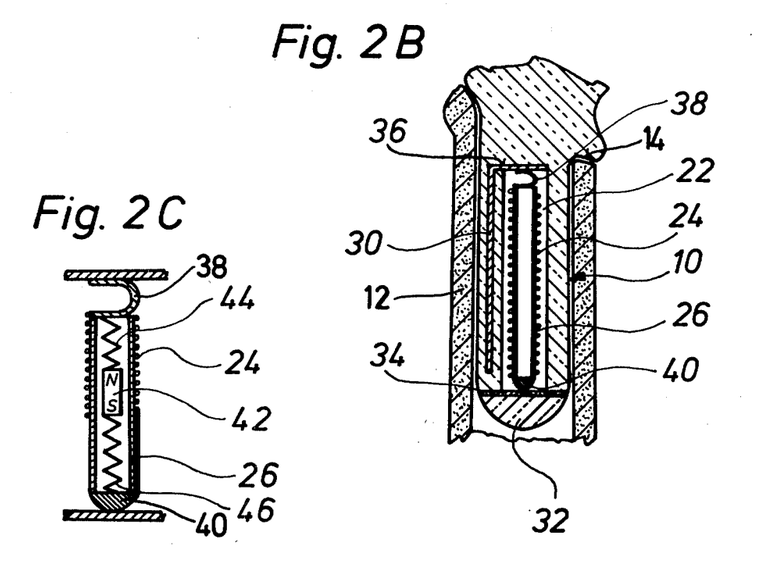
FIG. 2B shows a longitudinal section in a plane B—B of FIGS. 1 and 2A.
FIG. 2C shows a view, corresponding to FIG. 2B, of a modified embodiment.

In FIGS. 1, 2A and 2B as a first embodiment of the invention a hip joint head prosthesis is represented. It can for example consist of tissue-compatible aluminum oxide ceramic material and has a shank 10, which is mounted in a suitably truncated femur 12. The shank 10 is adjoined by an abutment surface 14 and a conventional joint head part 16.

The shank 10 is provided externally with axially extending ribs 18, between which groove-like depressions 20 are provided. Furthermore the shank 10 has a cavity 22, in which a cylindrical coil 24 is located, which is wound on a tubular coil core 26.

On the surface of the shank there are two electrodes 28 and 30, which respectively have a comb-like row of strip or finger-like projections, which are so arranged that the projections in the two electrodes alternate along the periphery of the shank. The cavity 22 is accessible by a cap 32, which is connected by a layer 34, produced by brazing, of tissue-compatible metal with the main part of the shank 10. The layer of brazing metal or spelter is insulated or made of the same metal, for example osteosynthetic metal, as the electrodes, so that no galvanic element is produced. The spelter layer 34 forms a part of the electrode 28 and is connected with the strip-like projections 28a of this electrode, which in the case of the embodiment actually shown are located on the ribs 18. The projections 28a can be produced by deposition from vacuum, metallization, electroplating or any other known ceramic metallization method and preferably extend somewhat into the side walls of the depressions 20 so that a continuous electrical connection is ensured even if a part of the metal layer located on one rib 18 should be frictionally worn away or otherwise damaged on driving the shank 10 into the bone. The projections 30a of the electrode 30 also consist of metallic layers and are located on the bottoms of the depressions 20. They are either individually, or as shown in FIG. 2B, by means of an annular metallized zone connected via holes 36, filled with electrically conducting material, with the interior of the cavity 22. At this position the ends of the cylindrical pick-up coil 24 make contact via a spring 38 or, respectively, a metal part 40 arranged at the end of the coil core 26, with the electrodes 30 and 28 respectively.

In the cylindrical pick-up coil 24 it is possible, as is indicated in the initially mentioned publications, to induce a low frequency electrical voltage, using an external coil supplied with AC and the induced voltage is effective at the electrodes 28 and 30 and promotes the embedding or "growing-in" of the shank 10 into the femur 12 and later prevents devitalization of the bone structure adjacent to the shank of the prosthesis.

For the automatic production of a weak alternating voltage between the electrodes 28 and 30 it is possible, as indicated in FIG. 2C, to arrange in the coil core 26 a rod-shaped permanent magnet 42 engaged by two relatively weak helical springs 44 and 46 and arranged so that they can move axially. In the axial direction of the cylindrical pick-up coil 24 the turn density varies or, as is indicated in FIG. 2C, only occupies a part of the range of movement of the permanent magnet 42. Owing to the inertial forces which come into play on walking and other movements of the wearer of the prosthesis the permanent magnet 42 performs axial movements in the coil core 26 and such movements automatically produce the desired low alternating voltage in the cylindrical pick-up coil 24. The system comprising the springs and the magnet should preferably have an inherent frequency of not more than 20 Hz.

Figures 3, 3A, 4, 5:
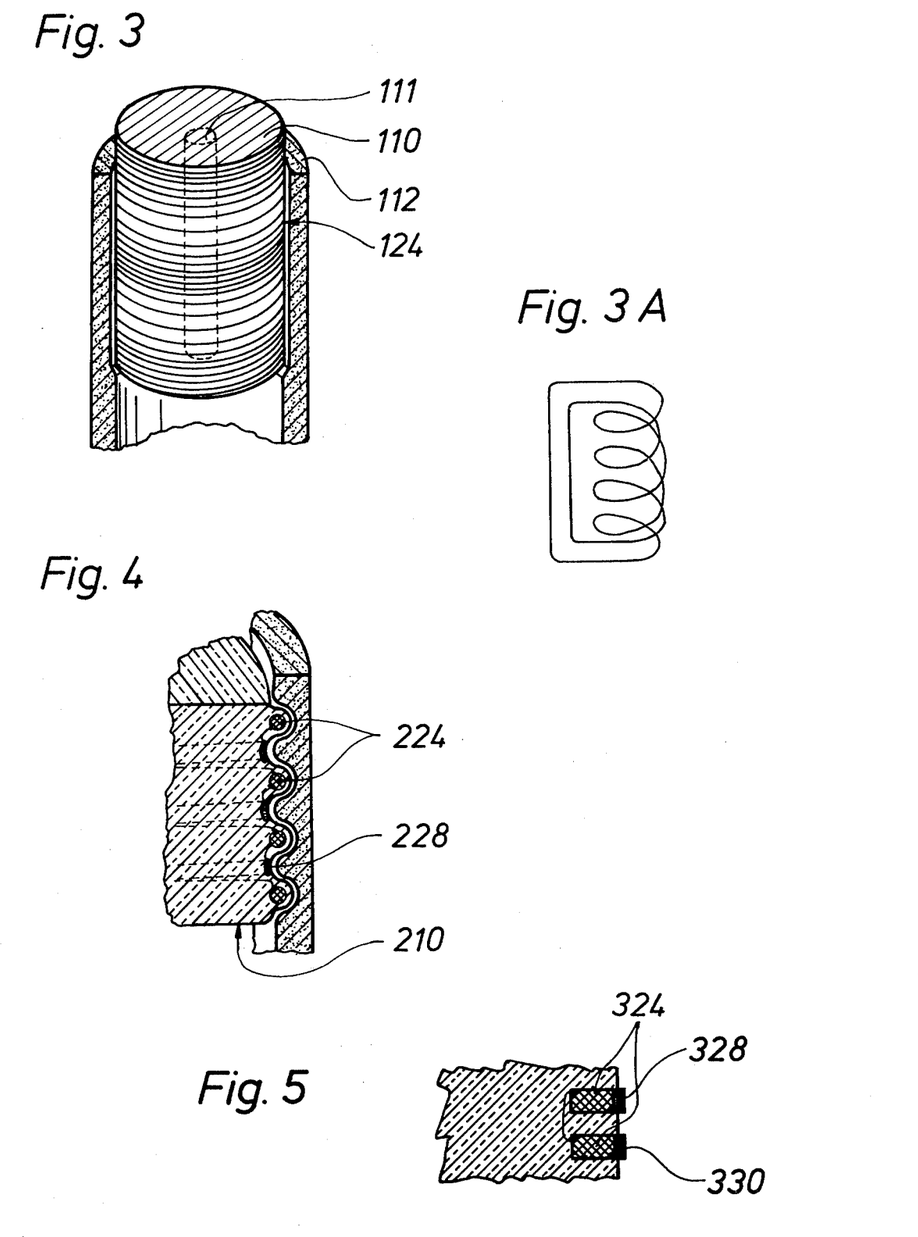
FIG. 3 shows a diagrammatic view of the shank part of an endoprosthesis in accordance with a further embodiment of the invention.
FIG. 3A shows a circuit diagram of a winding and electrode arrangement for the embodiment in accordance with FIG. 3.
FIG. 4 shows a part view of a shank part of an endoprosthesis of the type shown in FIG. 3.
FIG. 5 shows a view, corresponding to FIG. 4, with a somewhat modified coil and electrode arrangement.

FIG. 3 shows diagrammatically a shank 110 of an endoprosthesis, for example of a joint prosthesis, which like the shank 10 (FIG. 1) can consist of a tissue-compatible ceramic material. The ceramic shank 110 comprises an embedded rod-like core 111 of ferromagnetic material with a low coercive force as for example of a "magnetically weak" ferrite. On the substantially cylindrical outer surface of the shank 110 there is a coil deposited from vapor, whose turns simultaneously serve as electrodes. The coils can form a two-start screw and be electrically connected in series, as is represented in FIG. 3A, so that between two adjacent coils a voltage difference in accordance with the voltage is present, which is induced in one of the two helical coil parts connected in series. The clearance between turns of the coil 124 formed in this manner can, as represented, be uneven in order to produce higher field strengths in the part where there is a greater pressure loading between the bone 112 and the prosthesis shank than in zones where there is a lower loading.

FIG. 4 shows a part of a prosthesis shank 210, which has embedded windings 224 and embedded or deposited electrodes 228, which are respectively connected with corresponding turns of the winding 224. The outer side of the shank 210 can, as represented, be constructed as a screw. If the electrodes are embedded the ceramic material lying between the embedded electrodes and the surface of the shank is preferably made semi-conducting by the implantation of doping materials (see for example German Pat. (Offenlegungsschrift) No. 1,939,267). The arrangement of electrodes in different planes has the advantage, as is the case with the embodiment of FIGS. 1 and 2, that radial voltage gradients are produced, which promote the growth of axially aligned bone structure.

As is shown in FIG. 5 in the implant shank annular grooves can be provided, in which disc windings 324, connected in series, are accommodated. One respective coil of each disc winding is connected electrically with an externally placed electrode 328, 330 etc.

A radial field gradient can also be produced by providing two electrodes with a radial spacing and which are separated by a relatively coarse-pored layer of ceramic material. The surface of this layer then therefore carries one electrode, for example in the form of a perforated layer, while the other electrode is located at the bottoms of the pores. Such a structure can be produced by applying, for example by sintering on, on a ceramic body firstly a perforated but coherent layer of metallic particles and then a perforated layer of ceramic in such a manner that a part of the metallic particles is accessible through the holes and the ceramic material produces by virtue of the holes in the metallic layer a firm connection with the underlying ceramic material. The surface of the porous layer is then provided with a metallic layer forming the second electrode.

Figure 6:
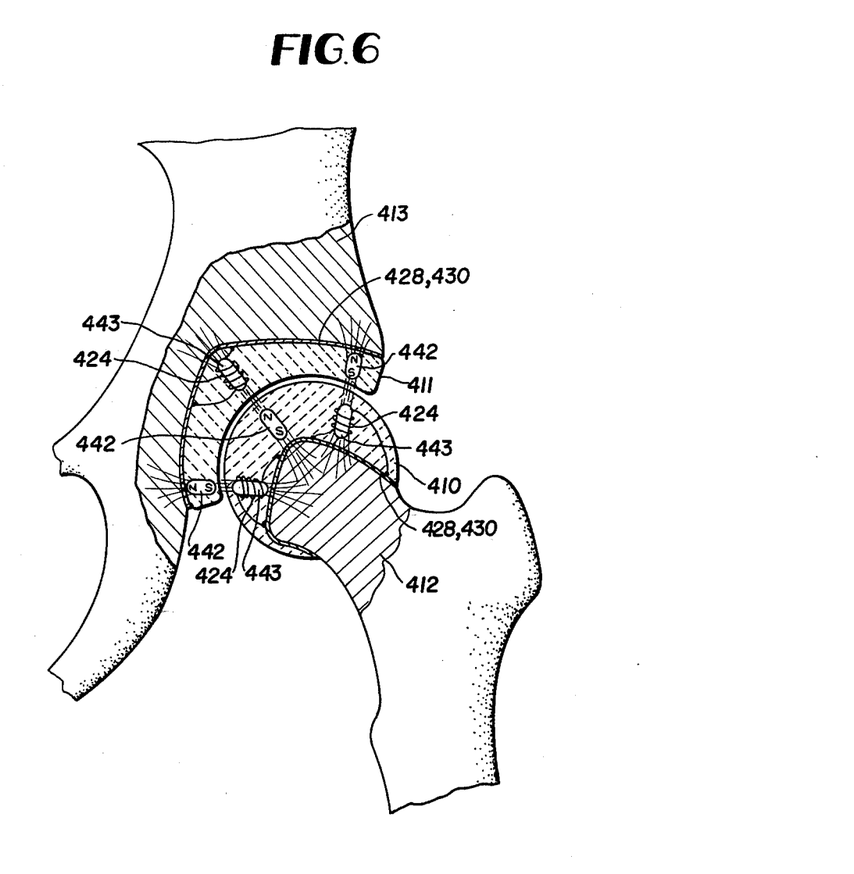
FIG. 6 shows a partly sectioned elevation of a hip joint prosthesis in accordance with one embodiment of the invention.
Figure 6A:
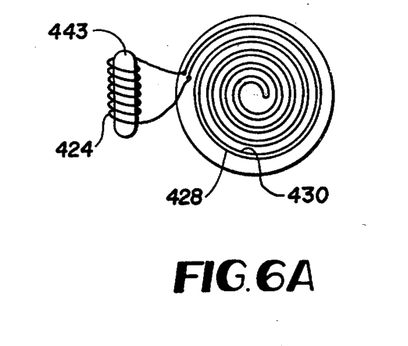
FIGS. 6A and 6B show diagrammatic views of receiving coils and electrode arrangements for the hip joint prosthesis in accordance with FIG. 6.

FIG. 6 shows a hip joint prosthesis, which consists of a ceramic part spherical cap 410 and a joint socket 411 of ceramic material. The ceramic part spherical cap 410 is mounted on a femur neck process 412. The joint socket 411 is implanted in the hip bone 413. In the ceramic part spherical cap 410 and the joint socket 411 rod-shaped permanent magnets 442 are arranged together with mutually opposite coils 424, which comprise rod-shaped magnetic cores 443 of magnetically soft material. In each case one respective permanent magnet 442 lies opposite to a coil 424 with a softly magnetic core 443. The ends of the coils 424 are respectively connected with electrodes 428 and, respectively, 430 (FIG. 6A). One such electrode arrangement is respectively arranged on the inner side, which is in contact with the femur neck process 412, of the ceramic part spherical cap 410 or, respectively, with the opposite, which is in contact with the bone 413, of the joint socket 411. In the case of the embodiment as shown in FIG. 6 the ceramic part spherical cap 410 comprises two coils 424; these coils can be connected in series or respectively connected with their own electrode sets. The electrodes 428 and 430 form two spirals which are interleaved and are electrically insulated from each other. The spacing between the spirals can be selected in accordance with the load distribution as has already been explained with reference to FIG. 3.

Figure 6B:
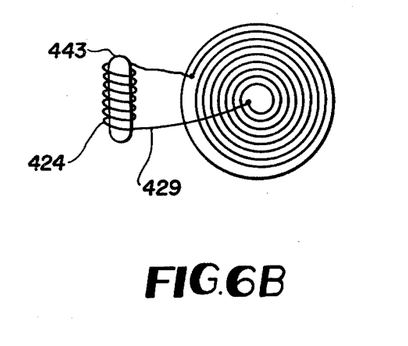

Instead of two separate electrodes it is also possible to use one single spiral winding, as is represented in FIG. 6B. The return conductor 429 intersecting the turns of the spiral is, just as is the case with the return conductor of the coils in accordance with FIG. 3A, insulated from the turns in a suitable manner, for example by an intermediate layer deposited from vapor of silicon dioxide or by the construction as an "entrenched" conductor. In the case of FIG. 6B the voltage between the individual turns of the spiral is effective.

If during the use of the hip joint prosthesis in accordance with FIG. 6 the permanent magnets are displaced with respect to the coils, the magnetic flux extending through the coils is changed and as a result a corresponding voltage is induced in the coils, which becomes effective at the electrodes and this prevents devitalization (encapsulation) of the zone areas which are in contact with the prosthesis parts.

The hip joint prosthesis in accordance with FIG. 7 has a hip head part 510, whose shank can be so constructed as already explained with reference to FIGS. 1 to 2C. The joint head part 516 in this case however comprises several radially arranged rod-shaped permanent magnets 542 and in the joint socket 511 there is a number of coils 524 embedded in such a manner that the magnetic flux produced by the ferromagnets in the coils changes during natural movement of the joint and as a result a corresponding voltage is produced in the coils. One permanent magnet can be provided with several coils as is represented by the coils 524a and 524b. The coils can naturally comprise magnetic cores with a high permeability and a low coercive force as is the case with the embodiment in accordance with FIG. 6.

The outer side of the joint socket 511 is again provided with electrodes which are supplied by the coils. The electrodes 528 and 530 can have projections, which, as is shown in FIG. 7A, extend radially and are interleaved in an alternating manner. As FIG. 7B shows the electrodes can also have the shape of eccentrically interfitting rings in the case of which adjacent electrodes are connected with different coil ends. In the area with the greatest mechanical loading the electrode spacing is at a minimum.

The low frequency alternating voltage, which is produced by a receiving coil and is supplied to an electrode arrangement, can have imposed on it a low direct voltage of for example a few tenths of a volt. This can be carried out as is shown for example in FIG. 7C, by arranging a parallel circuit arrangement of a semi-conductor diode, as for example a germanium diode 529 and a capacitor 531 in the lead extending from a receiving coil 525 to an electrode system as for example the electrode system 528, 530 in accordance with FIG. 7A or an electrode system as shown in FIG. 6A or FIG. 7B. The receiving coil 525 is so dimensioned, taking into account the threshold voltage of the semi-conductor diode, that at the electrode system a direct voltage of, at the most, a few tenths of a volt is produced and the capacitor 531 is so dimensioned that at the electrodes the desired alternating voltage of a few tenths of a volt results.

Figure 8A:
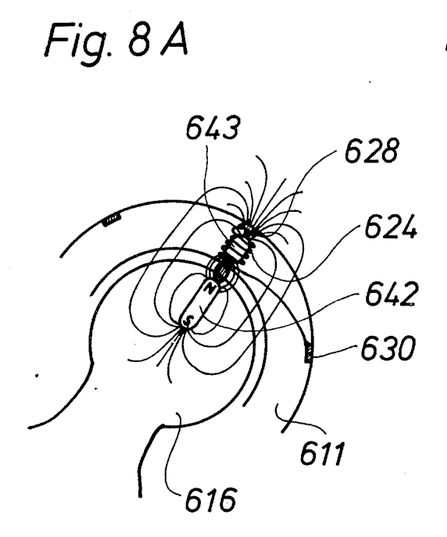
FIGS. 8A and 8B show diagrammatically the manner of operation of hip joint prosthesis of the type shown in FIGS. 6 and 7.
Figure 8B:
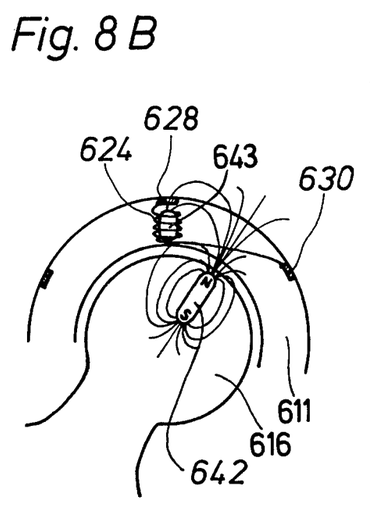

FIGS. 8A and 8B show diagrammatically how the voltage of the electrodes can be produced. The hip joint head part 616 comprises a radially arranged rod-shaped permanent magnet 642. The joint socket 611 comprises a cylindrical pickup coil 624 with a radial axis, about which a magnetic core 643 with a high permeability is wound. The ends of the coil are connected with electrodes 628 and 630 respectively. On movement of the joint with respect to the joint socket conditions alternate in which the permanent magnet 642 is directly opposite to the coil 624 (FIG. 8A) and, respectively, in which between the permanent magnet and the coil a relatively large spacing is present (FIG. 8B). The magnetic flux extending through the coil varies accordingly between a high and a low value and as a result a corresponding voltage is induced in the coil, which via the surface electrodes is applied at the tissue.

Figure 9:
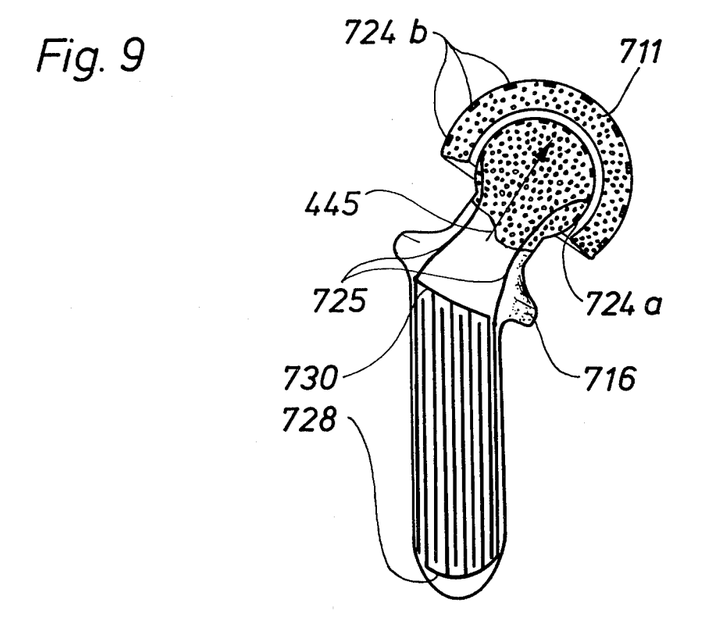
FIG. 9 shows a partly sectioned side view of a further hip joint prosthesis in accordance with the invention.

FIG. 9 shows an embodiment of a hip joint prosthesis in accordance with the invention with a hip head part 716 and a joint socket part 711. Both consist of ceramic material, in which granules of magnetically soft and magnetically hard material are embedded. The joint head is provided with a vapor deposited or embedded winding 724a, which is connected via embedded conductors 725 with electrodes 728 and 730, which can be constructed in accordance with FIG. 1.

The outer side of the joint socket 711 carries a winding 724b, which is joined together at its ends. The granules can have a diameter of for example 0.5 to 1 mm and are sintered in the ceramic material. The magnetically hard granules are magnetized by a magnetic field pulse, preferably in the axial direction of the joint head part (arrow 445). On movement of the joint head with respect to the joint socket in this case as well voltages are induced in turns. However it is possible to induce voltages in the turns also using an external magnetic alternating field with a high efficiency, since the magnetically soft granules concentrate the field and operate as a magnetic core for the windings.

Figure 10:
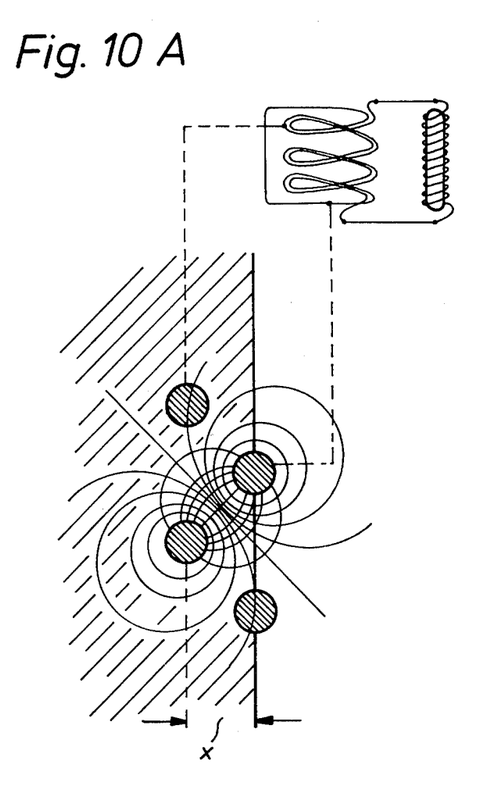
FIGS. 10A and 10B show preferred electroded arrangements.

FIG. 10A shows the electrical field distribution of a winding arrangement, which comprises two "bifilar" winding parts lying at different levels and which in a manner similar to the arrangement shown in FIG. 3A, are connected in series with a coil winding. The distance X between the surfaces, in which the winding parts are placed, does not in practice need to be very large and it can for example be equal to half or two thirds of the turn pitch or it could, as a further possibility, only comprise a few microns.

FIG. 10B shows a corresponding winding arrangement with windings, which have a rectangular profile. The windings, electrodes and other metal parts coming into contact with the tissue can for example be made of a platinum-iridium alloy.

Figure 11:
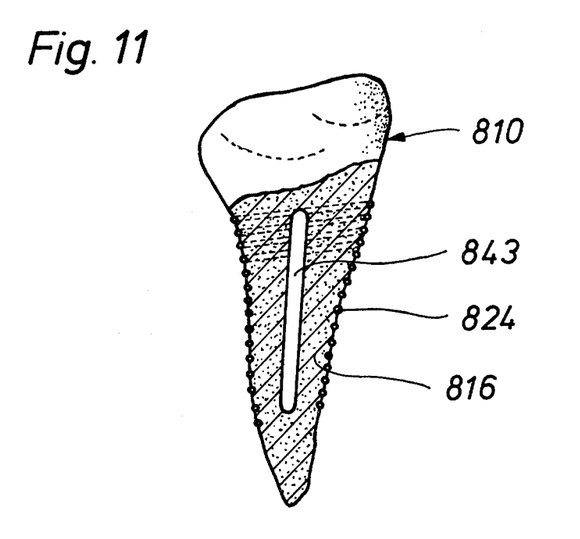
FIG. 11 shows a partly sectioned side view of a tooth prosthesis in accordance with the invention.

FIG. 11 shows a tooth prosthesis 810 of ceramic material which comprises an embedded magnetic core 843 of high permeability and low coercive force. The root part 816 of the tooth prosthesis, which is embedded in the jaw bone bears on its outer surface a coil winding 824, which can be constructed like the coils described with reference to FIGS. 3, 3A, 4 and 5 and FIGS. 10A and 10B and simultaneously serves as an electrode.

Figure 12:
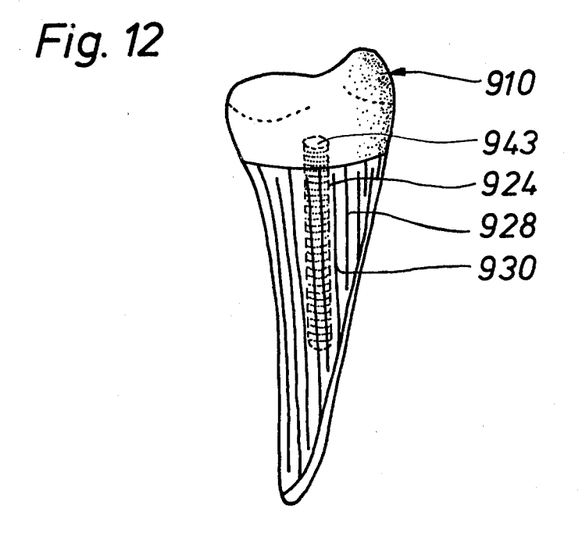
FIG. 12 shows an elevation of a further embodiment of a tooth prosthesis in accordance with the invention.

FIG. 12 shows a tooth prosthesis 910, in which a cylindrical pick-up coil 924 is embedded with a soft magnetic core 943. The ends of the cylindrical pick-up coil 943 are connected, in a manner similar to that shown in FIGS. 1 and 2 with comb-like interfitting electrodes 928 and 930 electrically.

Figures 7, 7A, 7B:
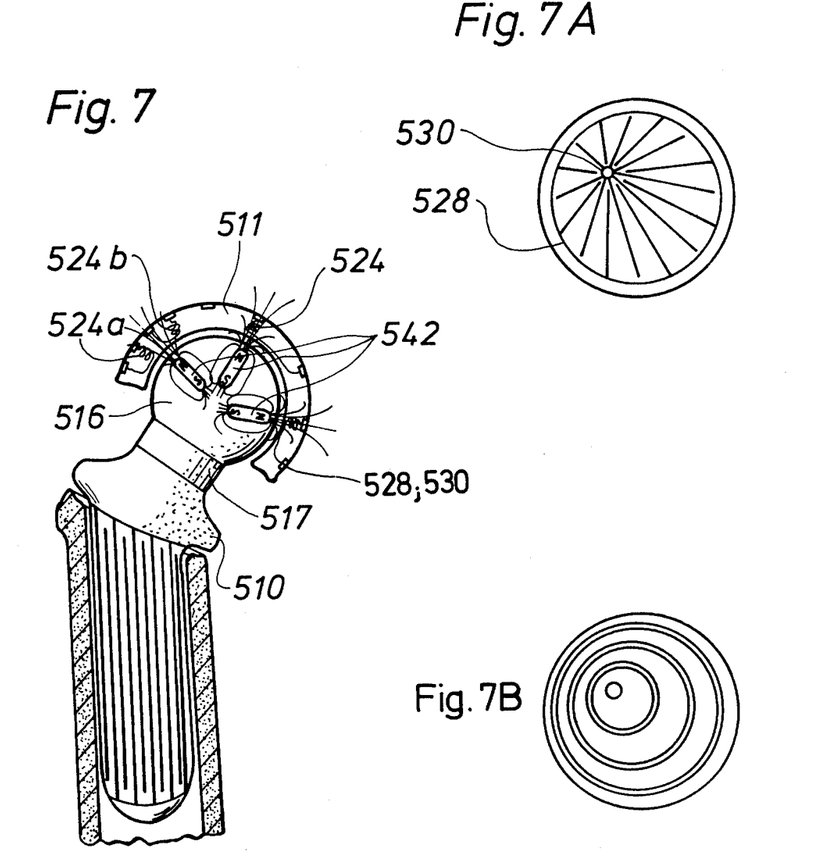
FIG. 7 shows diagrammatically another hip joint prosthesis in accordance with the invention.
FIGS. 7A and 7B show plan view of electrode arrangements for a hip joint prosthesis of the type shown in FIG. 7.
Figure 7C:
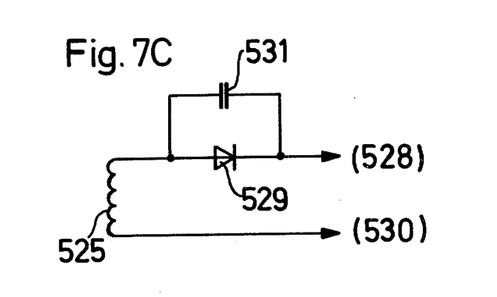
FIG. 7C shows a circuit arrangement for electrode arrangements as represented for example in FIGS. 6A, 7A and 7B.

If in the upper and lower jaws two mutually opposite or at least approximately mutually opposite dental prosthesis are to be provided, they can be equipped, in a manner similar to the hip joint prosthesis in accordance with FIGS. 6 to 8, with permanent magnet coil combinations for producing a voltage.

It is possible to produce the voltages necessary for the electrodes also by a piezoelectric effect. Thus for example a part of the implant, which during use is subjected to alternating loads, can be made of piezoelectric ceramic material or it can be provided with a piezoelectric element, which is electrically coupled with the electrodes and supplies the latter with an electric voltage changing with the mechanical load. Thus for example in the connection between the joint head part 516 and the shank part 510 a disc 517 of piezoelectric ceramic material can be arranged and fixed in position by brazing and the voltages produced on loading can be conducted away by a suitable insulated conductor system and supplied to the electrode system of the shank.

The ribs 18 of the prosthesis shank 10 (FIGS. 1 and 2) can also have a triangular, chevron-like cross-section.

I claim:

1. A long-term endoprosthesis comprising, in combination, a body member for implanting in the bone of a person, said body member having an outer surface configured for intimate contact with the bone in which said body member is implanted, a conductor wound on said body member having turns disposed in closely spaced relationship within the major portion of the area of contact between said body member outer surface and the bone, and means for coupling said wound conductor to an associated source of alternating electric power to produce an electomotive force in said wound conductor resulting in a voltage difference between the turns of said wound conductor at least some of the turns of said wound conductor being adapted to form electrodes for enhancing the growth of new bone in said area of contact, said associated source of alternating electric power comprising a permanent magnet movable with respect to said wound conductor forming said electrodes.

2. A long-term endoprosthesis in accordance with claim 1 wherein said endoprosthesis comprises two parts adapted to move relative to each other, one of said parts comprising at least one of a permanent magnet and a coil, the other of said parts comprising at least one coil adapted to operate with at least one of the permanent magnet of said first part and a permanent magnet adapted to cooperate with the coil of said first part.

3. A long-term endoprosthesis in accordance with claim 1 including at least one piezo electric element, means for coupling said at least one piezo electric element to said electrodes whereby on use of the prosthesis said piezo electric element is subjected to alternating loading to produce a voltage difference between said electrodes.

4. A long-term endoprosthesis in accordance with claim 1 wherein said electrodes are dispersed throughout at least 50 percent of said area of contact.

5. A long-term endoprosthesis in accordance with claim 1 wherein the spacing between adjacent electrodes has a maximum of 10 mm.

* * * * *